United States Patent
Kitajima

[19]

[11] Patent Number: 5,865,829

[45] Date of Patent: *Feb. 2, 1999

[54] MEDICAL OPTICAL APPARATUS

[75] Inventor: Nobuaki Kitajima, Tokyo, Japan

[73] Assignee: Kabushiki Kaisha Topcon, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 559,802

[22] Filed: Nov. 17, 1995

Related U.S. Application Data

[63] Continuation of Ser. No. 75,236, Jun. 14, 1993, abandoned.

[30] Foreign Application Priority Data

Jun. 15, 1992 [JP] Japan .................................. 4-155420
May 13, 1993 [JP] Japan .................................. 5-111274

[51] Int. Cl.⁶ ...................................................... A61B 3/12
[52] U.S. Cl. .......................... 606/3; 606/2; 606/4; 606/13; 607/88; 359/376; 359/351; 600/473; 600/476
[58] Field of Search .................................... 128/633, 634, 128/664–666, 654, 657; 606/2–4, 6, 7, 9–18; 607/88–93; 359/368–377, 351; 600/473–476

[56] References Cited

U.S. PATENT DOCUMENTS

| | | | |
|---|---|---|---|
| 3,796,220 | 3/1974 | Bredemeier | 606/18 |
| 4,556,057 | 12/1985 | Hiruma et al. | 128/665 |
| 4,594,608 | 6/1986 | Hatae et al. | 606/2 |
| 4,604,992 | 8/1986 | Sato | 606/11 |
| 4,817,622 | 4/1989 | Pennypacker et al. | 128/664 |
| 4,854,691 | 8/1989 | Sekine et al. | |
| 4,913,142 | 4/1990 | Kittrell et al. | 606/15 |
| 5,400,791 | 3/1995 | Schlier et al. | 128/664 |

FOREIGN PATENT DOCUMENTS

| | | | |
|---|---|---|---|
| 3148748 | 7/1983 | Germany | 606/5 |
| 3424995A1 | 1/1985 | Germany | |
| 3623394A1 | 2/1987 | Germany | |
| 3818084A1 | 12/1988 | Germany | |

*Primary Examiner*—David M. Shay
*Attorney, Agent, or Firm*—Finnegan, Henderson, Farabow, Garrett & Dunner, L.L.P.

[57] ABSTRACT

A medical optical system includes an observation optical system for guiding light emitted from a light source to a predetermined part to be illuminated, and causing light reflected from the predetermined part to be incident on the observation optical system. The medical optical system further includes a light separator, a guide optical system, and a display unit. The light separator is disposed at an intermediate part of the observation optical system, for separating the reflected light into reflected light of a visible observation wavelength area to be passed therethrough and reflected light or fluorescent light of the other wavelength area to be extracted therefrom. The guide optical system guides the light separated and extracted by the light separator to an image pick-up device so that an image of the separated light is formed on the image pick-up device. And the display unit displays the separated light image picked up by the image pick-up device.

7 Claims, 11 Drawing Sheets

(a)

(b)

(c)

(a)

(b)

MEDICAL OPTICAL APPARATUS

This application is a continuation of application Ser. No. 08/075,236, filed Jun. 14, 1993, now abandoned.

BACKGROUND OF THE INVENTION

1. Field of the Invention

This invention relates to a medical optical apparatus which uses a plurality of light each having a different wavelength.

2. Description of the Prior Art

As examples of surgical operation using a medical optical apparatus such as a medical microscope, there are cerebral surgical operation and ophthalmological operation. The ophthalmological operation includes an operation to be made on a bottom part of a vitreous body (i.e., vitreous body operation). The bottom part of the vitreous body is of a multi-layer structure having layers of a retina, a chorioidea and a sclera arranged in this order from the vitreous body.

For operation of this vitreous body, three holes, called ports, are formed in a side portion of an eye to be tested (patient's eye). One of these three ports is used for maintaining an intraocular pressure, another one of the remaining two ports is used for insertion of an optical fiber for illumination, and the last one is used for insertion of an operating instrument. For operation, the retina at the bottom part of the vitreous body is illuminated by the optical fiber and an objective part (diseased part) of the retina is operated using the operating instrument while observing the illuminated diseased part through a medical microscope.

A visible light is usually used for illumination during such operation. However, since the visible light is absorbed by the upper skin (or epithelium) layer of the retina, the patient's diseased part under the retina cannot be observed during the operation. Since only the visible light is used for observation of the bottom part of the eye to be tested, observation is limited. For observation of an inner side of the upper skin (or epithelium) layer of the retina, it can be contemplated that a fluorescent agent is injected into the patient's vein to send the fluorescent agent to a blood vessel of an eye fundus, and on the other hand, fluorescent excitation light is irradiated to the eye fundus so that the fluorescent excitation light is absorbed by the fluorescent agent which is still remained in or already leaked out of the blood vessel of the eye fundus, in order to excite the fluorescent agent, and then, the fluorescent light from the fluorescent agent is observed to check the diseased part in the upper skin (or epithelium) layer of the retina. This fluorescent observation is performed under a visible fluorescent light or an infrared fluorescent light. In this case, it is preferable that the visible fluorescent excitation light, the infrared fluorescent excitation light, the visible illumination light, and the infrared illumination light can be switched to one another so that the light can be selectively irradiated to the eye fundus or several kinds of light can be irradiated to the eye fundus simultaneously. In the medical optical apparatus such as a medical stereoscopic microscope, an illumination light from an illumination light source is projected to an observation part through an illumination optical system, and an image to be observed formed by the light reflected from this observation part is guided to an ocular lens through two main optical paths of the observation optical system, so that the operator can observe the observation part (for example, operating part, etc.) by his two eyes.

It is also necessary for an assistant operator to be able to observe the observation part in the same manner as the operator because the operation is cooperatively performed by the operator and the assistant operator. To this end, the medical stereoscopic microscope is provided with a sub-observation optical system branched from a midway of one of the main optical paths so that the assistant operator can also observe the observation part during the operation.

In a recent method of a medical treatment, it becomes more frequent to use an infrared light or light of a wavelength area low sensitive or hardly sensitive to a human eye such as a wavelength of about 400 nm or 700 nm (the light in this wavelength area is generally referred to as "invisible light"). For example, in a department of cerebral surgery, a malignant tumor is extracted by utilizing the nature of the fluorescent substance liable to selectively remain in a cancerous cell, or in an ophthalmological department, a deep layer of the retina is optically solidified by utilizing an infrared laser beam of light in order to arrest the progress of the patient's disease.

Heretofore, the optical solidification operation is performed while observing the diseased part under the visible light. However, since the human eye is not sensitive to an invisible light, it is usually difficult to observe the diseased part by naked eyes under this invisible light.

In order to observing the diseased part under this invisible light, it can be contemplated that a part of the reflected light from the observation part is extracted from the other optical path of the main observation optical system and guided to, for example, a TV camera sensitive to an ultraviolet light and a TV camera sensitive to an infrared light, so that the observation part is taken by the TV camera and displayed on a monitor TV.

SUMMARY OF THE INVENTION

It is therefore an object of the present invention to provide a medical optical system in which an inner part (intraocular part) of a predetermined part of a diseased eye can be observed using light of a wavelength necessary for observing and treating the inner part.

To achieve the above object, according to the present invention, there is provided a medical optical system comprising an observation optical system for guiding light from a light source to a predetermined part to illuminate it, a reflected light from the predetermined part being made incident to the observation optical system, the medical optical system further comprising light separation means disposed at an intermediate part of the observation optical system and adapted to pass therethrough a reflected light of a visible observation wavelength area among all reflected light from the predetermined part and separate a reflected light or fluorescent light of other wavelength areas to extract it, guide optical system adapted to guide the separated light by the light separation means to image pick-up means so that an image of the separated light is formed on the image pick-up means, and display means for displaying the separated light image picked up by the image pick-up means.

The invention further comprises displayed-image guiding optical system for guiding the separated light image displayed on the display means to an ocular lens.

The invention further comprises light separation means disposed at an intermediate part of the observation optical system and adapted to pass therethrough light of a wavelength of a visible predetermined part image among the reflected light from the predetermined part and separate light of a wavelength of a fluorescent light image to extract it, a fluorescent light guiding optical system for guiding the fluorescent light image wavelength light separated by the light separation means to image pick-up means so that the fluorescent light image is formed on the image pick-up means, display means for displaying the fluorescent light image picked up by the image pick-up means, and displayed-image guiding optical system for guiding the fluorescent light image displayed on the display means to the ocular lens of the observation optical system.

In another aspect of the invention, the light separation means is provided between an objective lens and an imaging lens of the observation optical system, and the displayed-image guiding optical system has a quick return mirror removably placed between the light separation means and the imaging lens.

In another aspect of the invention, the plurality of light sources include a white illumination light source for emitting a white illumination light and an infrared illumination light source for emitting an infrared excitation light. In the invention as claimed in claim 11, the plurality of light sources include a visible laser light source and an infrared laser light source having different wavelengths for specifically illuminating the predetermined part.

At least one of the visible laser light source and the infrared laser light source is controlled by a control circuit to selectively emit an aiming light having a low level emitting intensity for specifically illuminating the predetermined part and a laser treatment light having a high level emitting intensity in order to be used for treating the predetermined part.

The plurality of light sources include a white illumination light source for emitting a white illumination light and an infrared illumination light source for emitting an infrared excitation light, the illumination light from the illumination light sources being guided to the predetermined part by an illumination optical fiber, the plurality of light sources including a visible laser light source and an infrared laser light source specifically illuminating the predetermined part, the laser beam from the laser light source being guided to the predetermined part by a laser optical fiber, the medical optical system further comprising a control circuit for actuating or lighting up the visible laser light source when the white illumination light source is lighted up and also for lighting up the infrared laser light source when the infrared illumination light source is actuated or lighted up.

The plurality of light sources may include an illumination light source for illuminating the predetermined part and a laser light source for treating the predetermined part, the illumination light from the illumination light source being guided to the predetermined part by the illumination optical fiber, the laser beams from the plurality of laser light sources being guided to the predetermined part by the laser optical fiber, a part of the illumination light from the illumination light source being extracted by light guide means in order to be used as an aiming light for specifically illuminating a predetermined treating part by the laser light sources.

According another aspect of the invention, there is provided a medical optical system for illuminating an intraocular part of a patient using an optical fiber, the optical fiber being a single optical fiber for guiding light from a plurality of light sources to a predetermined part, the light from the plurality of light sources being guided to the single optical fiber by an optical path split member.

In the invention, light of at least two different wavelengths maybe projected onto the intraocular part of the patient using a single optical fiber.

These and other objects, features and advantages of the present invention will be well appreciated upon reading of the following description of the invention when taken in conjunction with the attached drawings with understanding that some modifications, variations and changes of the same could be made by the skilled person in the art to which the invention pertains without departing from the spirit of the invention or the scope of claims appended hereto.

BRIEF DESCRIPTION OF THE ATTACHED DRAWINGS

DESCRIPTION OF THE PREFERRED EMBODIMENTS

Figure 1:
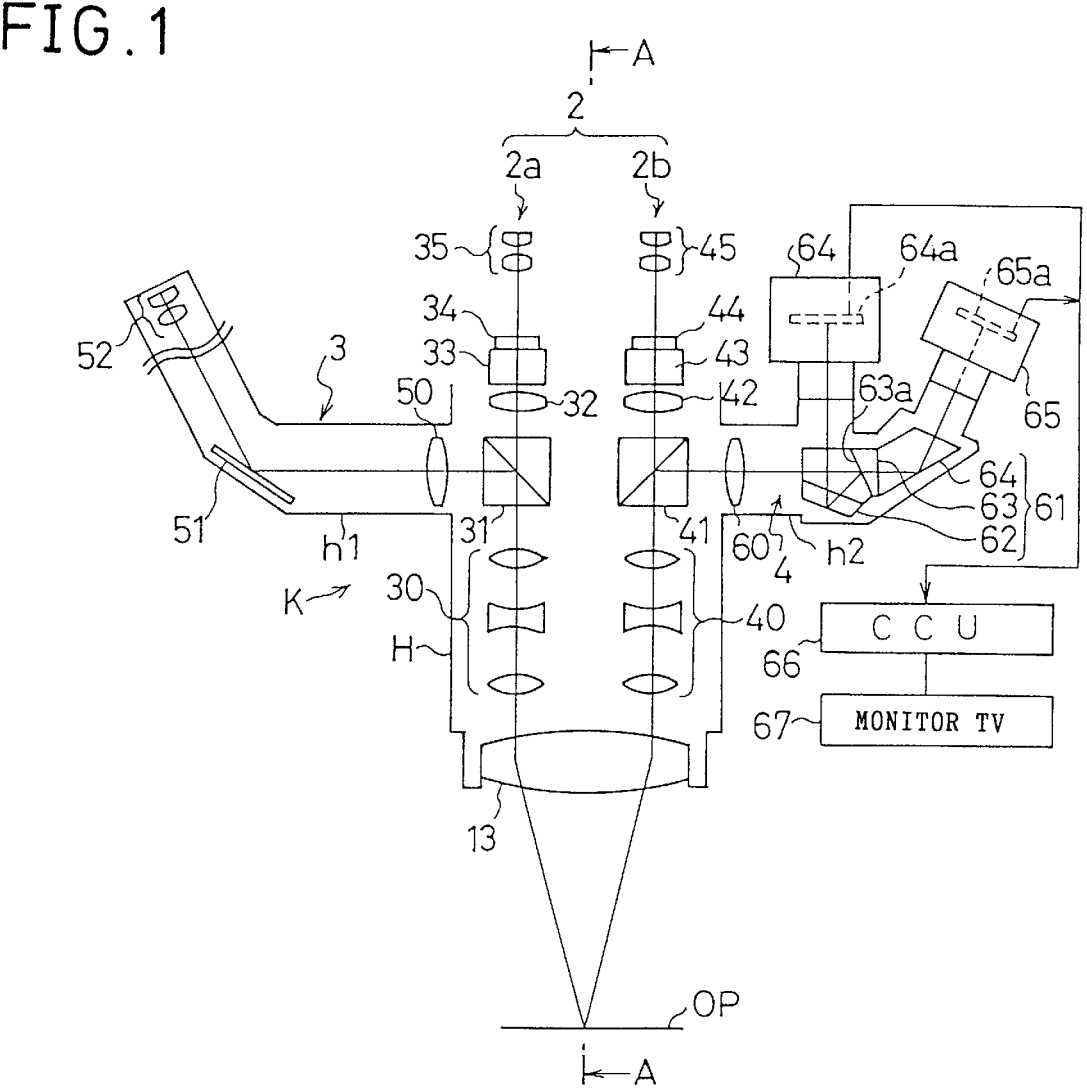
FIG. 1 is a schematic explanatory view showing one example of an optical system of a medical stereoscopic microscope of the present invention.

Embodiments of the present invention will be described hereinafter with reference to the accompanying drawings.
[First Embodiment]
In FIGS. 1 and 2, reference character OP denotes an observation part such as, for example, an eye fundus of an eye to be tested, an operating part or the like, and reference character K denotes a medical stereoscopic microscope for observing the observation part. The medical stereoscopic microscope K includes an illumination optical system 1 which is disposed within a housing H (see FIG. 2), a main observation optical system 2, a sub-observation optical system 3 (see FIG. 1), and an electronic image pick-up optical system 4.

The illumination optical system 1 includes an observation photographing illumination system 1a, and a photographing illumination system 1b. The observation photographing illumination system 1a includes a halogen lamp 10, an illumination lens 11, a prism 12, and an objective lens 13 all arranged in this order. An illumination light coming from the halogen lamp 10 illuminates the observation part OP through the illumination lens 11, the prism 12, and the objective lens 13. Emission of light from the halogen lamp 10 is controlled by a CCU (control circuit unit) or control circuit 66.

The photographing illumination system 1b includes a mercury xenon lamp 20, a light guide 21, an exciter filter 22 for passing therethrough only an excitation light of 650 nm, a focusing lens 23, a quick return mirror 24, the prism 12, and the objective lens 13 all arranged in this order. The exciter filter 22 passes an infrared light therethrough. Upon depression of a button (not shown), a control circuit 66 actuates a solenoid S to insert the quick return mirror 24 into a midway of an illumination optical system 1a, and then the halogen lamp 10 is deactivated, and emission of light from the mercury xenon lamp 20 is properly controlled.

When the solenoid S is actuated to insert the quick return mirror 24 into the midway of the optical path of the illumination optical system 1a as indicated by a solid line and the mercury xenon lamp 20 is caused to emit light in that condition, the illumination light from the mercury xenon lamp 20 is guided to the exciter filter 22 through the light guide 21. The exciter filter 22 allows only light of 650 nm to pass therethrough, and the light thus passed is irradiated to the observation part OP through the focusing lens 23, the quick return mirror 24, the prism 12, and the objective lens 13. As a result of this irradiation, a fluorescent substance existing on the observation part OP is excited to emit a fluorescent light longer than 650 nm.

The main observation optical system 2 includes a pair of opposing main optical paths, i.e., optical systems 2a and 2b so that observation can be made by two eyes. The optical system 2a includes the objective lens 13, a variable lens 30, an eye width adjusting diamond prism 34, and an ocular lens 35 all arranged in this order. The optical system 2b includes, as in the optical system 2a, the objective lens 13, a variable lens 40, a beam splitter 41, an imaging lens 42, an erect prism 43, an eye width adjusting prism 44, and an ocular lens 45 all arranged in this order.

An image to be observed, formed by the reflected light from the observation part OP, is observed by the operator's eyes through the pair of opposing optical systems 2a and 2b.

The housing H is provided at location corresponding to the beam splitters 31 and 41 with lens-barrel portions h1 and h2 each having a small diameter and projecting sidewardly. The lens-barrel portion h1 is provided therein with the sub-observation optical system 3, while the other lens-barrel portion h2 is Provided therein with the electronic image pick-up optical system 4.

The sub-observation optical system 3 includes a beam splitter 31, an imaging lens 50, a reflecting mirror 51, an optical member not shown, and an ocular lens 52. The image formed by the reflected light from the observation part OP is observed by the assistant operator through the objective lens 13, the variable lens 30, the beam splitter 31, the imaging lens 50, the reflecting mirror 51, the optical member not shown, the ocular lens 52, etc.

The electronic image pick-up optical system 4 includes the beam splitter 41, an imaging lens 60, and a wavelength separation prism 61 all arranged in this order. The wavelength separation prism 61 includes a roof prism 62, a wedge prism 63, and a trapezoidal prism 64 all cemented together.

Figure 3:
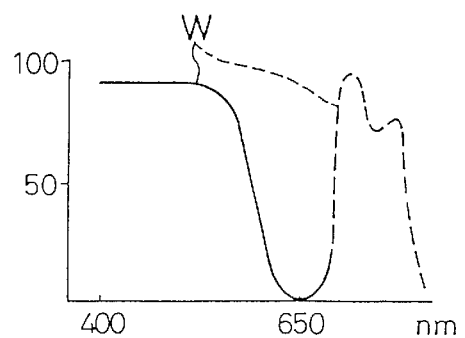
FIG. 3 is an explanatory view showing optical characteristics of a dichroic surface of FIG. 1.

On a cementing area between the roof prism 62 and the wedge prism 63, a dichroic surface 63a is formed. As shown by a characteristic curve W of FIG. 3, the dichroic surface 63a reflects light of a wavelength area below about 650 nm and passes light of a wavelength area above this. The light made incident to the wavelength separation prism 61 and reflected by the dichroic surface 63a is made incident to a color TV camera 64 to form an image to be observed on an area CCD 65a of an infrared TV camera 65.

The TV cameras 64 and 65 are firmly secured to the lens-barrel portion h2. The wavelength separation prism 61 is used as mentioned above for the purposes that the incident light to the TV cameras 64 and 65 are reflected even-numbered times and the TV cameras 64 and 65 are mounted closely adjacent the lens-barrel portion h2 so that the cameras 64 and 65 do not interfere with each other.

Image signals from the TV cameras 64 and 65 are inputted into a monitor TV 67 through a CCU (control circuit unit) or control circuit 66, and an image of the observation part is displayed by the monitor TV 67.

Next, the operation of the medical stereoscopic microscope thus constructed will be described.
(Observation under illumination by Illumination System 1a)

Figure 2:
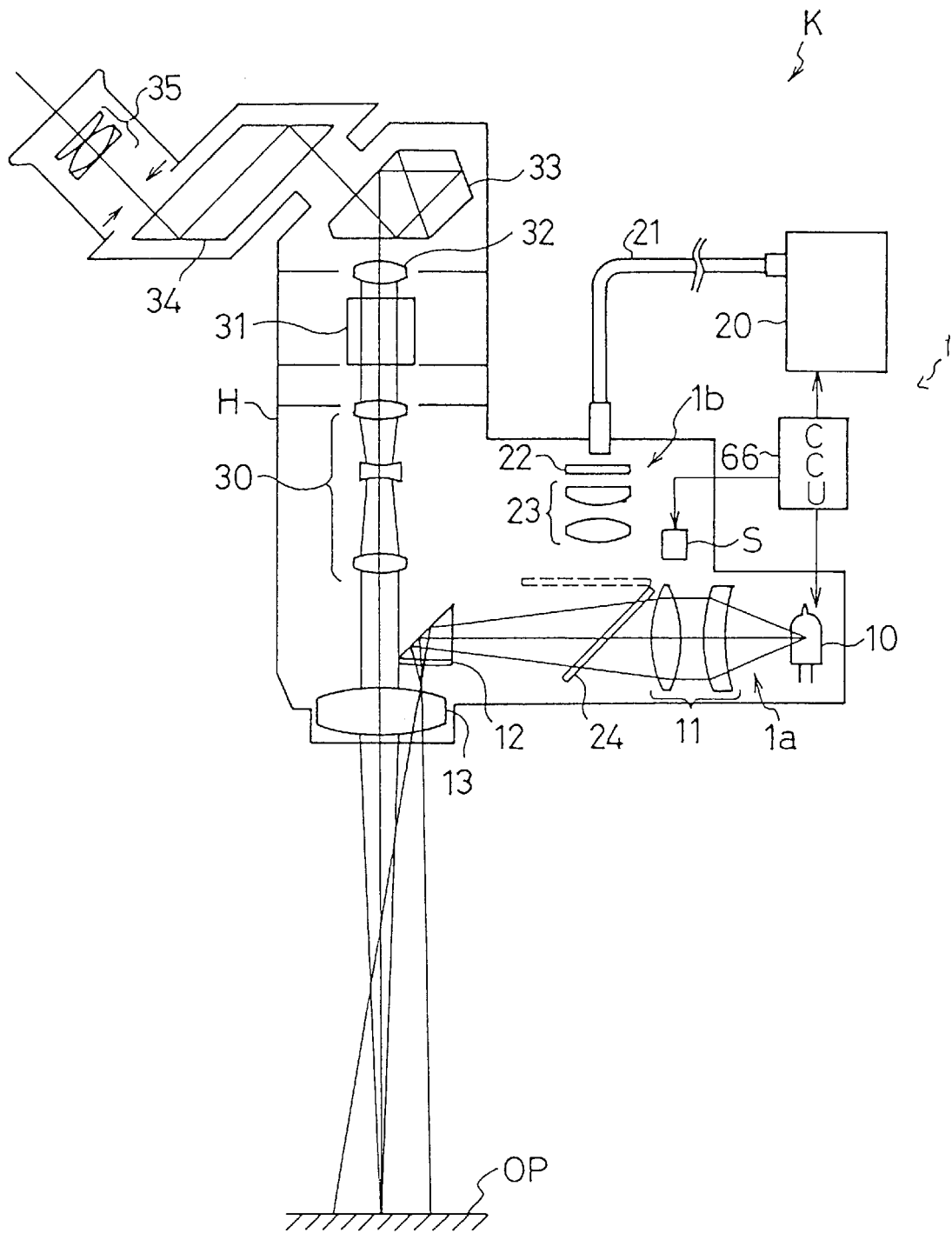
FIG. 2 is a schematic explanatory view of a stepped surface taken on line A—A of FIG. 1.

At normal observation, in the control circuit 66, the quick return mirror 24 is withdrawn outwardly from the optical path of the illumination system 1a as indicated by broken lines of FIG. 2, and the halogen lamp 10 is caused to emit light in that condition. The illumination light coming from the halogen lamp 10 illuminates the observation part OP through the illumination lens 11, the prism 12, and the objective lens 13. The image formed by the reflected light from the observation part OP is observed by the operator's two eyes through the pair of opposing optical systems 2a and 2b.

On the other hand, the reflected light from the observation part OP is made incident to the wavelength separation prism 61 through the objective lens 13, the variable lens 40, the beam splitter 41, and the imaging lens 60 Among the reflected light made incident to the wavelength separation prism 61, the visible light is reflected by the dichroic surface 63a and made incident to the color TV camera 64 to form an image to be observed on the area CCD 64 of the color TV camera 64.
(Photography under illumination by Illumination System 1a)

For photographing, a fluorescent agent, which absorbs the light of a wavelength of, for example, 650 nm and emits an excitation light above 650 nm, is injected into the vein of the patient.

When a taking switch not shown is turned on in that condition, the control circuit 66 actuates the quick return mirror 24 to insert the quick return mirror 24 into the intermediate portion of the optical path of the observation photographing illumination system 1a as indicated by the solid line, and thereafter the mercury xenon lamp 20 is caused to emit light.

The illumination light from the mercury xenon lamp 20 is guided to the exciter filter 22 through the light guide 21 and only the light of 650 nm is allowed to pass through the exciter filter 22 so as to be irradiated to the observation part OP via the focusing lens 23, the quick return mirror 24, the prism 12, and the objective lens 13. As a result of this irradiation, the fluorescent agent existing on the observation part of the patient is excited to emit a fluorescent light longer than 650 nm.

The reflected light (excitation light) and the fluorescent light from the observation part OP are made incident to the wavelength separation prism 61 through the objective lens 13, the variable lens 40, the beam splitter 41, and the imaging lens 60. The light of a wavelength of 650 nm made incident to the wavelength separation prism 61 is reflected by the dichroic surface 63*a* so as to be made incident to the visible TV camera 64.

On the other hand, the light of a wavelength above 650 nm made incident to the wavelength separation prism 61 is allowed to pass through the dichroic surface 63*a* and made incident to the infrared TV camera 65 to form an image to be observed on the area CCD 65*a* of the infrared TV camera 65. An image signal from this TV camera 65 is inputted into the monitor TV 67 through the CCU (circuit control unit) or control circuit 66, and as a result, an image of the observation part formed by the fluorescent light is displayed by the monitor TV 67.

If one sensitive to a wavelength below 650 nm is used as the area CCD 64*a* of the visible TV camera 64 and one for allowing a wavelength below 650 nm to pass therethrough is used as the exciter filter 22, the reflected light from the observation part OP is made incident to the wavelength separation prism 61, and the light having a wavelength below 650 nm made incident to the wavelength separation prism 61 is reflected by the dichroic surface 63*a* so as to be made incident to the visible TV camera 64, and as a result, an observation image is formed on the area CCD 64*a* of the visible TV camera 64. The image signal from this TV camera 64 is inputted into the monitor TV 67 through the CCU (control circuit unit) or control circuit 66, and a whole image of the observation part formed by the reflected excitation light is displayed on the monitor TV 67.

Accordingly, by combining the whole image formed by the TV camera 64 with the fluorescent light image formed by the TV camera 65, the position of the fluorescent light image can be known.

If the exciter filter 22 is omitted at the time when a photograph is taken, a color photograph can be taken by the visible TV camera 64 and an infrared light image is taken by the infrared TV camera 65.

[Second Embodiment]

Figure 4:
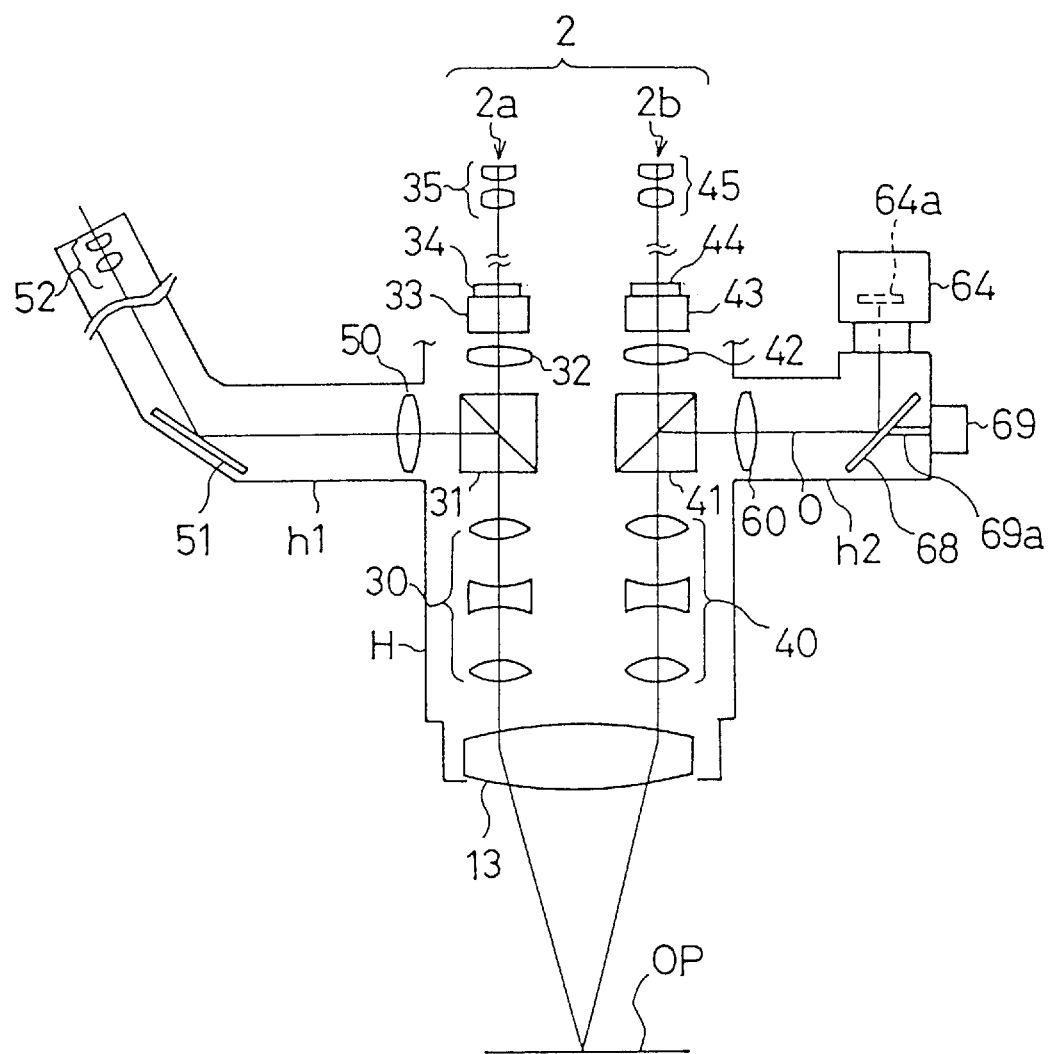
FIG. 4 is a schematic explanatory view showing another example of an optical system of a medical stereoscopic microscope of the present invention.
Figure 5:
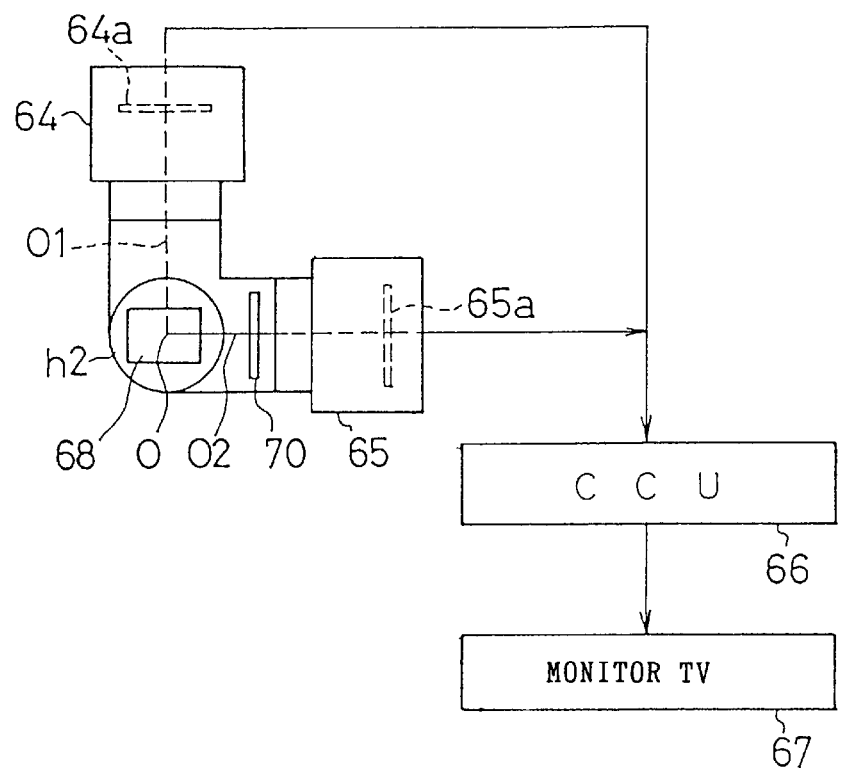
FIG. 5 is a right-hand side view of a TV camera portion of FIG. 4.
Figure 6:
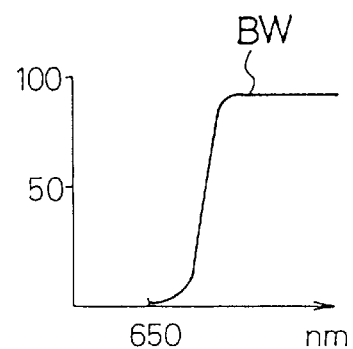
FIG. 6 is a chart showing an optical characteristic curve of a barrier filter of FIG. 5.

In the above-mentioned embodiment, although the visible light and the infrared light are separately guided to the TV cameras 64 and 65 using the wavelength separation prism 61, the present invention is not limited to this. For example, there may be employed the construction as shown in FIGS. 4 and 6.

In this embodiment, the color TV camera 64 and the infrared TV camera 65 are mounted on the lens-barrel portion h2 with the optical axes 01 and 02 of the color TV camera 64 and the infrared TV camera 65 and the optical axis 0 of the imaging lens 60 are intersected with each other at right angle. At an area where the optical axes 0, 01 and 02 within the lens-barrel portion h2, luminous flux guide means or slant mirror 68, instead of the wavelength separation prism 61, is disposed in such a manner as being pivotally operable about the optical axis 0. The slant mirror 68 is firmly secured to an output shaft 69*a* of a pulse motor 69 driving of which is controlled by the control circuit 66. Provided between the slant mirror 68 and the infrared TV camera 65 is a barrier filter 70 for allowing the light of a wavelength area above 650 nm as shown by the characteristic curve BW of FIG. 6 to pass therethrough. Upon depression of the button (not shown) of the first embodiment, the control circuit 66 causes the focusing lens 23 to be inserted into an intermediate portion of the optical path of the illumination system 1*a*. The halogen lamp 10 is turned off and emission of light of the mercury xenon lamp 20 is controlled. Then, the pulse motor 69 is actuated to direct the slant mirror 68 toward the infrared TV camera 65 so that the reflected light can be guided toward the infrared TV camera 65.

Then, the control circuit 66 withdraws the focusing lens 23 outwardly from the midway of the observation photographing illumination system 1*a* as indicated by the broken lines, deactivates the mercury xenon lamp 20 and activates the halogen lamp 10. Then, the pulse motor 69 is actuated to direct the slant mirror 68 toward the color TV camera 64 so that the reflected light can be guided toward the color TV camera 64.

[Third Embodiment]

In the embodiments so far described, the excitation light image of 650 nm reflected from the observation portion and the fluorescent light image emitted from the observation portion are taken by the TV cameras 64 and 65 respectively, and a combined image of these two images is displayed by the monitor TV 67, or otherwise the observation portion image formed by the visible light and the above fluorescent light image are taken by the TV cameras 64 and 65 respectively, and a combined image of these two images is displayed by the monitor TV 67. However, the present invention is not necessarily limited to these combinations.

For example, in the first embodiment, the dichroic surface 63*a* may be provided with an interference film so that the color image formed by the visible light and the ultraviolet light image formed by the infrared light can be taken by the two TV cameras 64 and 65, respectively. Alternatively, the dichroic surface 63*a* may be provided with the interference film so that the infrared light image formed by the infrared light and the ultraviolet light image formed by the ultraviolet light can be taken by the two TV cameras 64 and 65, respectively.

Figure 7:
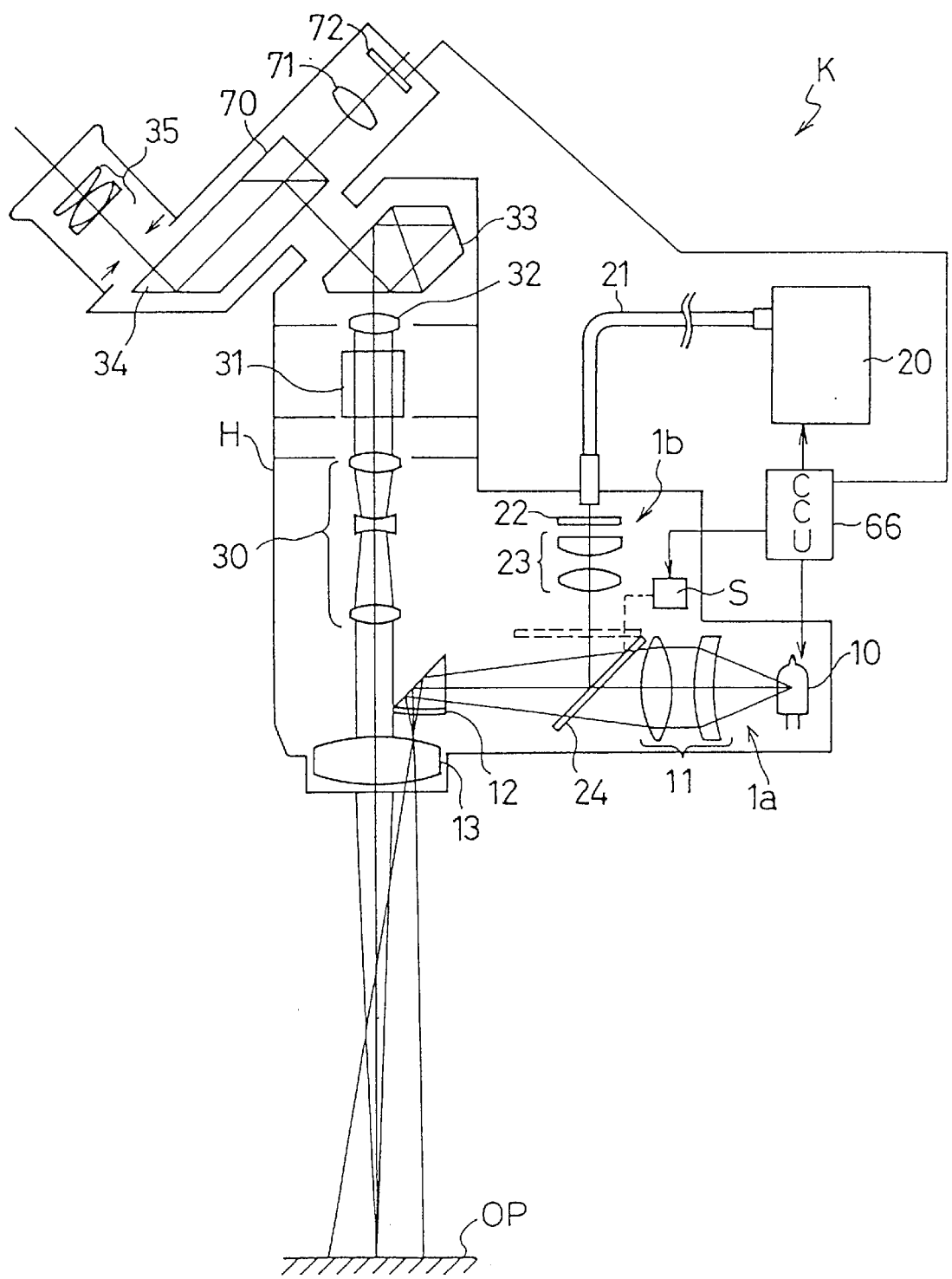
FIG. 7 is a schematic explanatory view showing a second embodiment of an optical system of a medical stereoscopic microscope of the present invention.

As shown in FIG. 7, there may be provided an inner side display system comprising a rectangular prism 70 cemented to an upper portion of the diamond prism 34, an imaging lens 71, and a color liquid crystal display 72, so that the same image as that of the monitor TV 67 can be displayed on the color liquid crystal display 72 by the control circuit 66. In this case, it may be arranged such that ON/OFF of the display can be made optionally by the operator through switching operation.

In the invention so far described, since the electronic image pick-up means comprises a plurality of electronic image pick-up elements each having a different wavelength sensitivity, even in the case where a wavelength which cannot be observed by naked eyes (for example, infrared light) is used, the observation part can be electronically observed.

[Fourth Embodiment]

<Construction of Medical Microscope>

<Construction of Operation Microscope>

Figure 8:
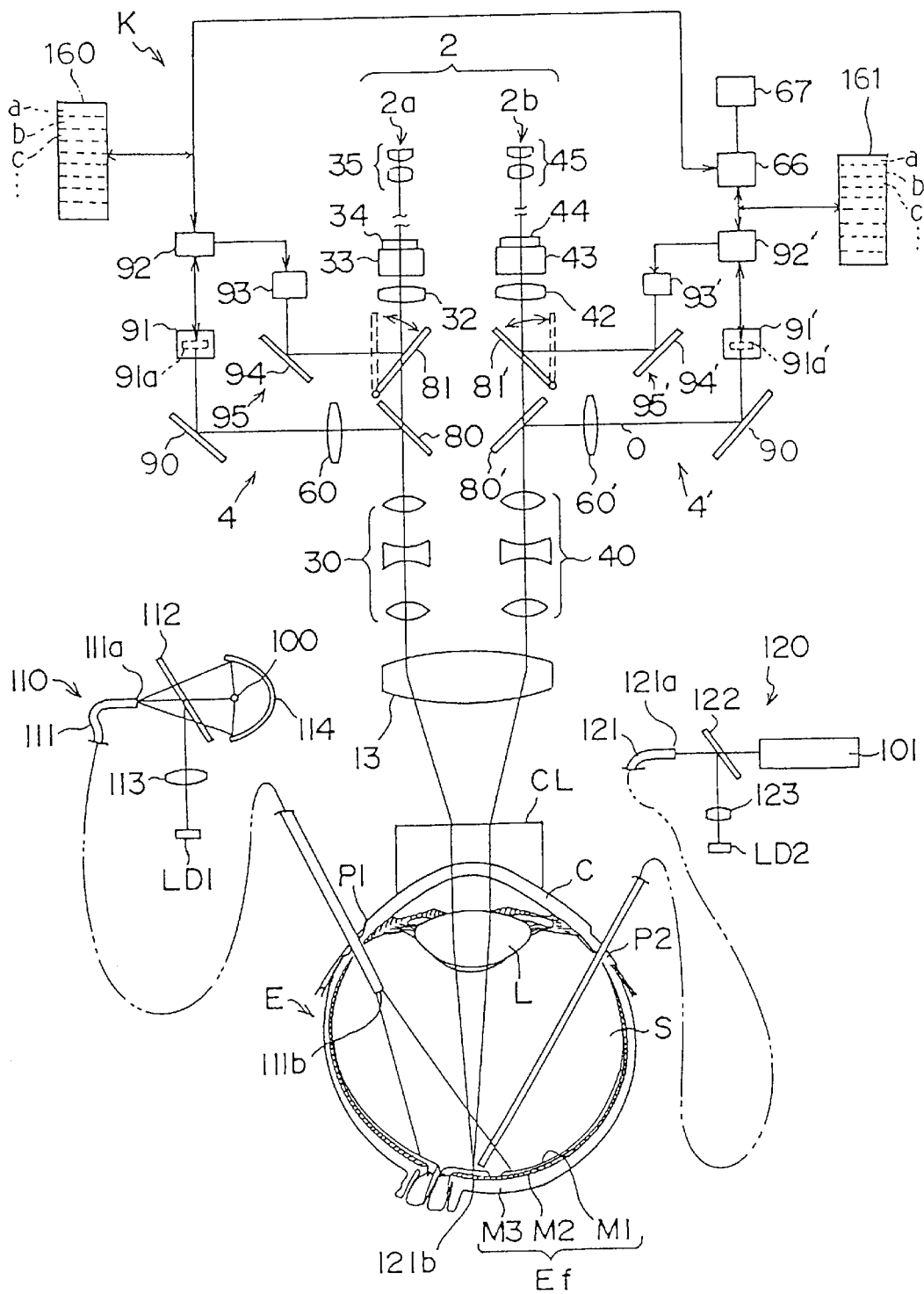
FIG. 8 is an explanatory view of an optical system showing a fourth embodiment of a medical optical system according to the present invention.

FIG. 8 shows a fourth embodiment of the present invention.

In FIG. 8, reference character E denotes an eye to be tested, reference numeral C denotes a cornea of the eye E, reference character L denotes a crystalline lens, reference character CL denotes a contact lens abutted with the cornea C, reference character S denotes a vitreous body of the eye E, and reference character Ef denotes a fundus (bottom part of the glass body) of the eye E. The eye fundus Ef (predetermined part) is of a multi-layer structure having layers of a retina M1, a chorioidea M2 and a sclera M3 arranged in this order.

Reference character K denotes a medical stereoscopic microscope for observing the observation part. This medical stereoscopic microscope K includes an observation optical system 2, and electronic image pick-up optical systems 4 and 4' (fluorescent optical systems). The observation optical system 2 includes a pair of opposing main optical paths r optical systems 2a and 2b so that the operator can observe the observation part by his two eyes.

The optical system 2a includes an objective lens 13, a variable lens 30, a dichroic mirror 80 (light separation means), a quick return half mirror 81, an imaging lens 32, an erect prism 33, an eye width adjusting diamond prism 34, and an ocular lens 35 all arranged in this order.

The optical system 2b includes, as in the optical system 2a, the objective lens 13, a variable lens 40, a dichroic mirror 80', a quick return half mirror 81', an imaging lens 42, an erect prism 43, an eye width adjusting prism 44, and an ocular lens 45 all arranged in this order.

Figure 10:
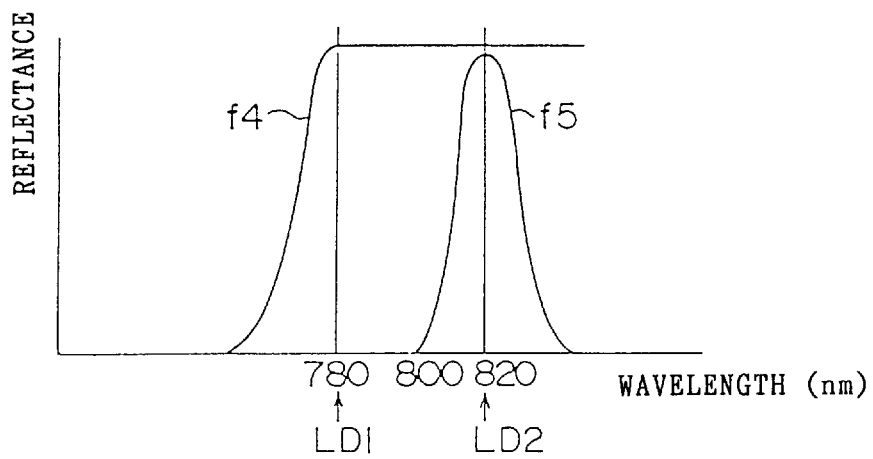
FIG. 10 is a chart showing a characteristic curve of a dichroic mirror of FIG. 8.

As shown by a curve f5 of FIG. 10, the dichroic mirrors 80 and 80' reflect the infrared light of a wavelength area whose central wavelength is 820 nm and whose width is about 40 nm and allow the visible light to pass therethrough. The image formed by the reflected light from the eye fundus Ef as the observation part is observed by the operator's two eyes.

The electronic image pick-up optical system (fluorescent light optical system) 4 includes the dichroic mirror 80, an imaging lens 60, and a slant mirror 90 all arranged in this order. The light reflected by the slant mirror 90 is made incident to an infrared fluorescent light image pick-up TV camera 91 to form the image to be observed on an area CCD 91a (image pick-up means) of the TV camera 91. Similarly, the other electronic image pick-up optical system (fluorescent light optical system) 4' includes the dichroic mirror 80', an imaging lens 60', and a slant mirror 90' all arranged in this order. The light reflected by the slant mirror 90' is made incident to the infrared fluorescent light image pick-up TV camera 91' to form the image to be observed on an area CCD 91a' (image pick-up means) of the TV camera 91'.

The image signals from the opposing TV cameras 91 and 91' are inputted respectively into image processing circuits 92 and 92'.

The image processing circuits 92 and 92' process the image signals from the TV cameras 91 and 91' and output picture signals respectively. The picture signals from the opposing image processing circuits 92 and 92' input the infrared fluorescent light data respectively into image memories 160 and 161 through a CCU (control circuit unit) or control circuit 66. This control circuit 66 builds up such picture data as an infrared fluorescent light image and an aiming spot light image in a Plurality of frame memories a, b, c, etc. of the image memory 160 in accordance with the picture signal from the left-hand side image processing circuit 92. Also, the control circuit 66 builds up such picture data as an infrared fluorescent light image and an aiming spot light image in a plurality of frame memories a, b, c, etc. of the image memory 161 in accordance with the picture signal from the right-hand side image processing circuit 92'.

The control circuit 66 displays the infrared fluorescent light images of the observation part coming from the TV cameras 91 and 91' on the opposing sides of the monitor TV 67 in accordance with the infrared fluorescent light image data from the image memories 160 and 161. On the other hand, the image signals from the image memories 160 and 161 are inputted respectively into liquid crystal displays 93 and 93' (display means) through the image processing circuits 92 and 92', and the infrared fluorescent light images (display images) are displayed on the liquid crystal displays 93 and 93', respectively.

The infrared fluorescent light image from the liquid crystal display 93 is guided to the ocular lens 35 via a display optical system 95 comprising a slant mirror 94, and a quick return half mirror 81, and also via the imaging lens 32, the erect prism 33, and the eye width adjusting diamond prism 34 of the optical system 2a. Similarly, the infrared fluorescent light image from the other liquid crystal display 93' is guided to the ocular lens 45 via a display image optical system 95' comprising a slant mirror 94', and a quick return half mirror 81', and also via the imaging lens 42, the erect prism 43, and the eye width adjusting diamond prism 44 of the optical system 2b.

<Construction of Light Irradiation System>

A light irradiation system includes a plurality of illumination light sources each having a different wavelength, and a plurality of aiming light sources each having a different wavelength.

Figure 9:
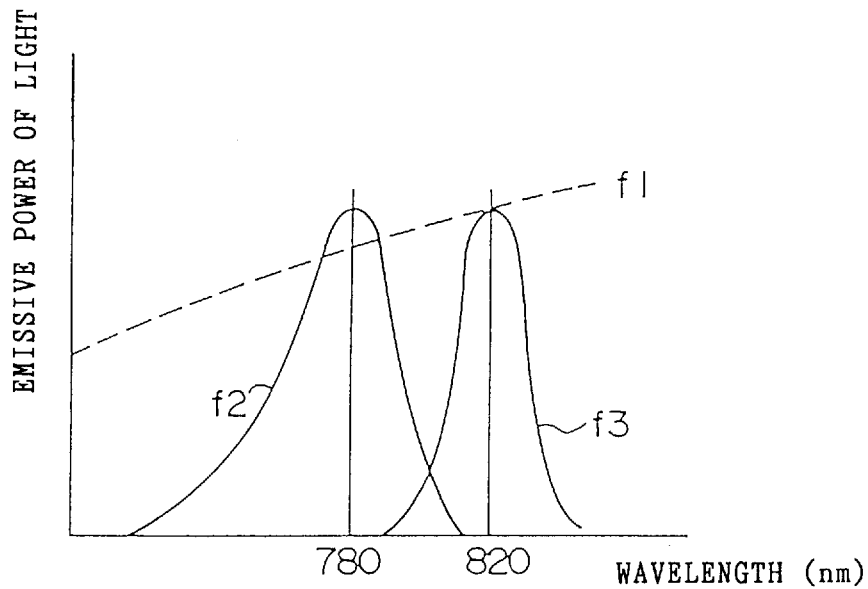
FIG. 9 is a chart of a characteristic curve showing a relation between an absorption spectrum and a light emitting spectrum of a halogen lamp and an ICG shown in FIG. 8.

As the illumination light sources, a halogen lamp 100 (white illumination light source or visible illumination light source) including a wavelength ranging from a visible area to an infrared area as shown by a curve f1 of FIG. 9, and a laser diode LD1 (infrared illumination light source or infrared laser light source) of an oscillating wavelength of 780 nm are used.

As the aiming light sources, an argon laser unit 101 (visible laser light source or visible illumination light source) of an oscillating wavelength of 514 nm, and a laser diode LD2 (infrared laser light source or infrared illumination light source) of an oscillating wavelength of 820 nm are used.

The light irradiation system includes an illumination optical system 110 for guiding illumination light from a plurality of illumination light sources to the eye to be tested, and an aiming optical system 120 for guiding light from a plurality of aiming light sources.

(Illumination Optical System 110)

The illumination optical system 110 includes an optical fiber 111 (light guiding fiber, illuminating fiber), a dichroic mirror 112 (optical path splitting member), a focusing lens 113, and a concave reflecting mirror 114. As shown by a curve f4 of FIG. 10, the dichroic mirror 112 reflects the light of an infrared wavelength area of a wavelength of 760 nm or above and allows a visible light to pass therethrough.

The illumination light from the halogen lamp 100 passes through the dichroic mirror 112 while being reflected and gathered by the concave reflecting mirror 114 so as to be made incident to one end 111a of the optical fiber 111. On the other hand, the laser beam from the laser diode LD1 is reflected by the dichroic mirror 112 while being gathered through the focusing lens 113, and then made incident to the one end 111a of the optical fiber 111.

The optical fiber 111 is inserted into a vitreous body S through a port P1 provided to a side portion of the eye E, and the illumination light made incident to the optical fiber 111 is irradiated toward the eye fundus Ef from the other end portion 111b in order to illuminate the eye fundus Ef.

(Aiming Optical System 120)

The aiming optical system 120 includes an optical fiber 121 (light guiding fiber, laser optical fiber), a dichroic mirror 122 (optical path splitting member), and a focusing lens 123. As shown by a curve f5 of FIG. 10, the dichroic mirror 122 reflects the light of a wavelength area whose central wavelength is 820 nm and whose width is about 40 nm and allows the visible light to pass therethrough.

The illumination light from the argon laser unit 101 is allowed to pass through the dichroic mirror 112 and made incident to one end 121a of the optical fiber 121. On the other hand, the laser beam from the laser diode LD2 is reflected by the dichroic mirror 122 while being gathered through the focusing lens 123, and then made incident to the one end 121a of the optical fiber 121.

The optical fiber 121 is inserted into the glass body S through a port P2 provided to a side portion of the eye E, and the illumination light made incident to the optical fiber 121 is irradiated toward the eye fundus Ef from the other end portion 121b in order to illuminate the eye fundus Ef.

<Control Circuit>

Figure 11:
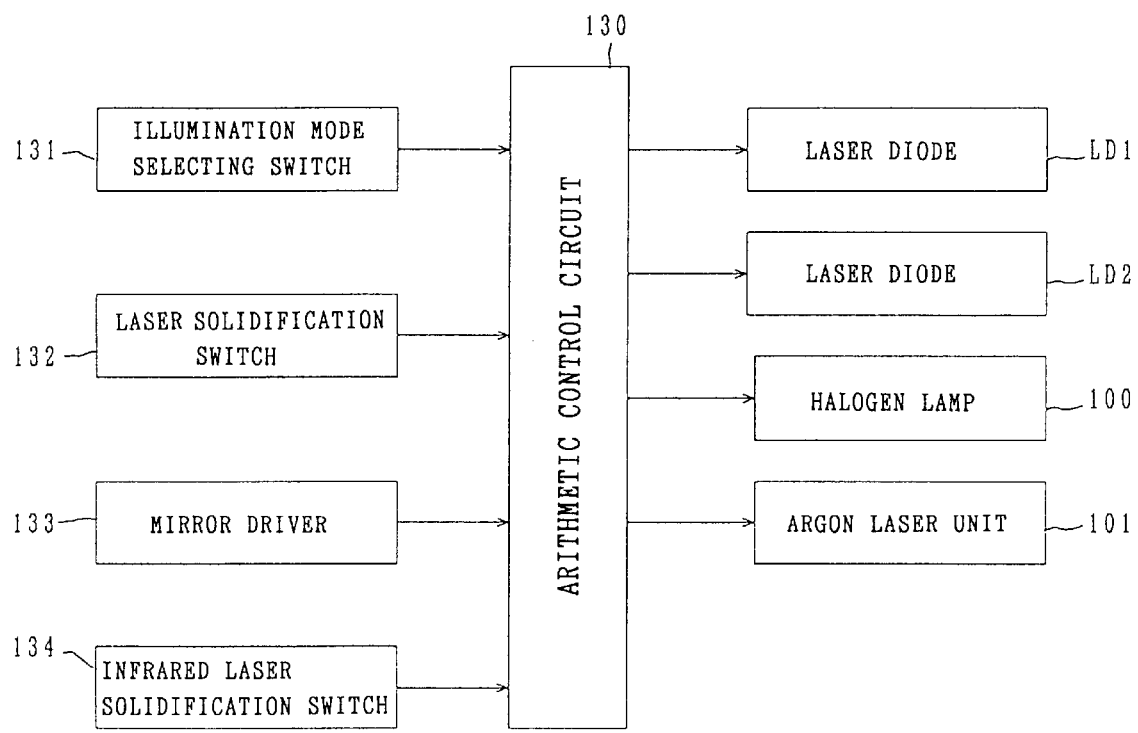
FIG. 11 is a diagram of a control circuit of an apparatus of FIG. 8.

The laser diodes LD1 and LD2, the halogen lamp 100, and the argon laser unit 101 are controlled by an arithmetic control circuit 130 of FIG. 11. Connected to the arithmetic control circuit 130 are an illumination mode selection switch 131, a laser solidification switch 132, and a mirror driver 133 for inserting and withdrawing the quick return half mirror 81 to and from the optical path.

Next, the operation of the operating apparatus thus constructed will be described.

(1) Visible Observation

When an illumination mode of visible light is selected by the illumination mode selection switch 131, the arithmetic control circuit 130 lights up the halogen lamp 100 and at the same time activates the argon laser unit 101 and also sets intensity of emission of light of the argon laser unit 101 to a low level. At this time, the arithmetic control circuit 130 controls the mirror driver 113 to withdraw the quick return half mirrors 81 and 81 from the intermediate portions of the optical paths of the optical systems 2a and 3a, respectively.

Thereafter, a distal end of the other end portion 111b of the optical fiber 111 is brought away from the eye fundus Ef of the eye E as shown in FIG. 8, and on the other hand, the other end portion 121b of the optical fiber 121 is brought closely to the treating part of the eye fundus Ef.

By doing this, the visible illumination light from the halogen lamp 100 is reflected by the concave reflecting mirror 114 and then allowed to pass through the dichroic mirror 112 so as to be made incident to the optical fiber 111. Then, it is irradiated toward the eye fundus Ef of the eye E from the other end portion 111b of the optical fiber 111 so as to illuminate a predetermined range of the eye fundus Ef.

On the other hand, the laser beam of a low level intensity of a wavelength of 514 nm emitted from the argon laser unit 101 is allowed to pass through the dichroic mirror 122 and then made incident to the optical fiber 121. Then, it is irradiated toward the eye fundus Ef from the other end 121b of the optical fiber 121 so as to illuminate the treating part of the eye fundus Ef.

A part of the visible reflected light from the eye fundus for illuminating the eye fundus Ef is guided to the ocular lens 35 via the vitreous body S, the crystalline lens L, the cornea C, the contact lens CL, the objective lens 13, the variable lens 30, the dichroic mirror 80, the imaging lens 32, the erect prism 33, and the eye width adjusting diamond prism 34. On the other hand, the remainder of the visible reflected light is guided to the ocular lens 45 via the vitreous body S, the crystalline lens L, the cornea C, the contact lens L, the objective lens 13, the variable lens 40, the dichroic mirror 80, the imaging lens 42, the erect Prism 43, and the eye width adjusting diamond Prism 44.

Figure 12:
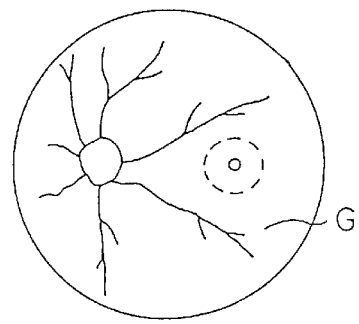
FIG. 12(a) is an explanatory view showing an eye fundus observation image under a visible light and an infrared fluorescent light of the apparatus of FIG. 8.
FIG. 12(b) is an explanatory view showing an eye fundus observation image under an infrared fluorescent light of FIG. 8.
FIG. 12(c) is an explanatory view when the images of FIGS. 12(a) and 12(b) are observed in superimposed condition.
Figure 12:
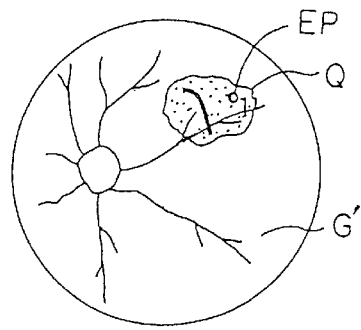
Figure 12:
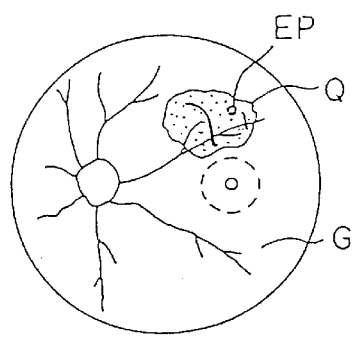

Therefore, by looking into the ocular lenses 35 and 45, the operator can stereoscopically see the illuminating part of the eye fundus Ef on an enlarged scale as shown in FIG. 12(a).

(2) Infrared Fluorescent light Observation

On the other hand, an ICG (Indo Cyanin Green) is injected to the vein of the patient.

When an illumination mode of the infrared excitation light is selected by the illumination mode selection switch 131, the arithmetic control circuit 130 lights up the laser diode LD1 with the halogen lamp 100 being lighted, and turns off the argon laser unit 101 and lights up the laser diode LD2. At this time, the arithmetic control circuit 130 controls the mirror driver 133 to insert the quick return half mirrors 81 and 81 into the intermediate portion of the optical paths of the optical systems 2a and 3a, respectively.

Thereafter, the distal end of the other end portion 111b of the optical fiber 111 is brought away from the eye fundus Ef of the eye E as shown in FIG. 8, and the other end portion 121b of the optical fiber 121 is brought closely to the treating part of the eye fundus Ef.

As a consequence, the visible illumination light from the halogen lamp 100 is reflected by the concave reflecting mirror 114 and then allowed to pass through the dichroic mirror 112 so as to be made incident to the optical fiber 111. Then, it is irradiated toward the eye fundus Ef of the eye E from the other end portion 111b of the optical fiber 111 so as to illuminate a predetermined range of the eye fundus Ef.

At this time, the infrared excitation light of 780 nm from the laser diode LD1 is irradiated to the eye fundus Ef through the focusing lens 113, the dichroic mirror 112, and the optical fiber 111. As a result, if the ICG injected into the vein of the patient has reached the capillary blood vessel, the infrared excitation light of 780 nm is absorbed by this ICG. As a result, the ICG is excited to emit an infrared fluorescent light of 800 nm or larger whose central wavelength is 820 nm. In FIG. 9, reference numeral f2 denotes an infrared light absorbing wavelength area of the ICG, and reference numeral f3 denotes a wavelength area of the infrared fluorescent light emitted from the ICG when excited by the infrared light of the wavelength f2.

On the other hand, the laser beam of a wavelength 820 nm emitted from the laser diode LD2 is irradiated to the eye fundus Ef through the focusing lens 123, the dichroic mirror 122, and the optical fiber 121 in order to illuminate (spot illumination) the treating part of the eye fundus Ef.

A part of the reflected light (visible illumination reflected light, infrared excitation reflected light, infrared fluorescent light, and infrared aiming reflected light) from the eye fundus for illuminating the eye fundus Ef is made incident to the optical system 2a of the operation microscope via the vitreous body S, the crystalline lens L, the cornea C, and the contact lens CL.

When an illumination mode of the infrared excitation light is selected by the illumination mode selection switch 131, it may be arranged such that the halogen lamp 100 is turned off so that only the infrared fluorescent light image can be observed. In this case, the quick return half mirror 81 may be replaced by a total reflection quick return mirror so that a clearer fluorescent light image can be observed.

(Optical System 2a)

The reflected light from the eye fundus Ef is guided to the dichroic mirror 80 through the objective lens 13, and the variable lens 30. Among the reflected light passing through the variable lens 30, the visible reflected light and the infrared excitation reflected light are caused to pass through the dichroic mirror 80 and the quick return half mirror 81, and then guided to the ocular lens 35 through the imaging lens 32, the erect prism 33, and the eye width adjusting diamond prism 34. As a result, the observer can observe the eye fundus blood vessel G as shown in FIG. 12(a) through the operation microscope.

On the other hand, among the reflected light passing through the variable lens 30, the infrared fluorescent light of 800 nm or above and the aiming reflected light are made incident to the TV camera 91 through the dichroic mirror 80, the imaging lens 60, and the slant mirror 90 so as to form an infrared fluorescent light image (image to be observed) and an aiming spot light image on the area CCD 91a (image pick-up means) of the TV camera 91.

The image signal from the TV camera 64 is inputted into the image processing circuit 92. This image processing circuit 92 processes the image signal from the TV camera 64 and outputs a picture signal. The picture signal from the image processing circuit 92 is inputted into the CCU (control circuit unit) or control circuit 66. This control circuit 66 builds up such picture data as an infrared fluorescent light image and an aiming spot light image in any of the frame memories a, b, c, etc. of the image memory 160 in accordance with the picture signal.

The control circuit 66 displays the infrared fluorescent light image of the observation part from the TV camera 91 on either of the opposing side of the monitor TV 67 in accordance with the picture data such as the infrared fluorescent light image and the aiming spot light image built up in the frame memories a, b, c, etc. of the image memory 160. On the other hand, the image signal from the TV camera 91 is inputted into the liquid crystal display 93 (display means) through the image processing circuit 92. As shown in FIG. 12(b), an eye fundus blood vessel image G' formed by the infrared fluorescent light, a fluorescent light image (display image) Q formed by leak from the chorioidea or the chorioidea blood vessel, and the aiming spot light image EP are displayed on the liquid crystal display 93. The eye fundus blood vessel image G', the fluorescent light image Q and the spot light image EP are superimposed on the eye fundus blood vessel image G of FIG. 12(b) and observed as shown in FIG. 12(c).

The infrared fluorescent light image from the liquid crystal display 93 is guided to the ocular lens 35 through the display image guiding optical system 95 comprising the slant mirror 94, and the quick return half mirror 81, the imaging lens 32, the erect prism 33, and the eye width adjusting diamond prism 34 of the optical system 2a.

(Optical System 2b)

Similarly, among the reflected light from the eye fundus Ef, the reflected light (visible illumination reflected light, infrared excitation reflected light, infrared fluorescent light, and infrared aiming reflected light) made incident to the optical system 2b is also guided, as in the case of the reflected light made incident to the optical system 2a, to the dichroic mirror 80' through the objective lens 13 and the variable lens 40. Among the reflected light from the variable lens 40, the visible reflected light and the infrared excitation reflected light are caused to pass through the dichroic mirror 80' and the quick return half mirror 81', and then guided to the ocular lens 45 through the imaging lens 42, the erect prism 43, and the eye width adjusting diamond prism 44. As a result, the observer can observe the eye fundus blood vessel image G as shown in FIG. 12(a) through the operation microscope.

On the other hand, among the reflected light passing through the variable lens 40, the infrared fluorescent light of 800 nm or above and the aiming reflected light are made incident to the other TV camera 91' through the other dichroic mirror 80', the imaging lens 60' and the slant mirror 90' so as to form an infrared fluorescent light image (image to be observed) on the area CCD 91a' (image pick-up means) of the TV camera 91'.

The image signal from this TV camera 91' is inputted into the other image processing circuit 92'. Then, the image processing circuit 92' processes the image signal from the TV camera 91' and outputs a picture signal. The picture signal of the image processing circuit 92' is inputted into the CCU (control circuit unit) or control circuit 66. Then, the control circuit 66 builds up such picture data as an infrared fluorescent light image and an aiming spot light image in any of the frame memories a, b, c, etc. of the image memory 161 in accordance with the picture signal.

The control circuit 66 displays the infrared fluorescent light image of the observation part from the other TV camera 91' on the remaining side of the monitor TV 67 in accordance with the picture data such as the infrared fluorescent light image and the aiming spot light image built up in the frame memories a, b, c, etc. of the image memory 161. On the other hand, the image signal from the TV camera 91' is inputted into the other liquid crystal display 93' (display means) through the image processing circuit 92. As shown in FIG. 12(b), an eye fundus blood vessel image G' formed by the infrared fluorescent light, a fluorescent light image (display image) Q and the aiming spot light image EP are displayed on the liquid crystal display 93'. The eye fundus blood vessel image G', the fluorescent light image Q and the spot light image EP are superimposed on the eye fundus blood vessel image G of FIG. 12(a) and observed as shown in FIG. 12(c).

The infrared fluorescent light image from the other liquid crystal display 93' is guided to the ocular lens 45 through the display image guiding optical system 95' comprising the slant mirror 94', and the other quick return half mirror 81', the imaging lens 42, the erect prism 43, and the eye width adjusting diamond prism 44 of the optical system 2b.

In this way, by building up the picture data of the eye fundus blood vessel image G' formed by the infrared fluorescent light, the fluorescent light image Q and the aiming light image EP in the image memories 160 and 161, the particular part can be observed in a superimposed condition, as shown in FIG. 12(c), merely by switching operation even when the aiming light is not available. The same image as this image is displayed on the monitor TV 67.

(3) Laser Solidification of Eye Fundus

By using the operation microscope having a construction of (1) or (2), the diseased part of the eye fundus Ef and the diseased part in the upper skin (or epithelium) layer of the retina can be stereoscopically observed. At this time, when separation of the retina and a lower part layer disease of the retina are confirmed, the aiming light is irradiated to the predetermined part under observation. In that condition, when the laser solidification switch 132 is turned on, the arithmetic control circuit 130 controls the intensity of the laser emission of the argon laser unit 101 to a level required for optical solidification of the eye fundus and causes the argon laser unit 101 to emit such laser beam. The optical solidification laser beam from the argon laser unit 101 is caused to pass through the dichroic mirror 122 and then made incident to the optical fiber 121. Then, it is irradiated toward the eye fundus Ef from the other end portion 121b of the optical fiber 121 so as to optically solidify (laser treatment) the treating part of the eye fundus Ef where the aiming light is irradiated. Further, when the infrared laser solidification switch 134 is turned on, the laser beam from the laser diode LD2 reaches a level of emission intensity of the laser beam required for optical solidification. As a result, the deep layer portion of the retina can be directly optically solidified.

[Fifth Embodiment]

In the embodiment so far described, when the eye fundus Ef is illuminated by the halogen lamp 100, the aiming light is irradiated to the treating part by the argon laser unit 101. However, the present invention is not limited to these embodiments.

Figure 13:
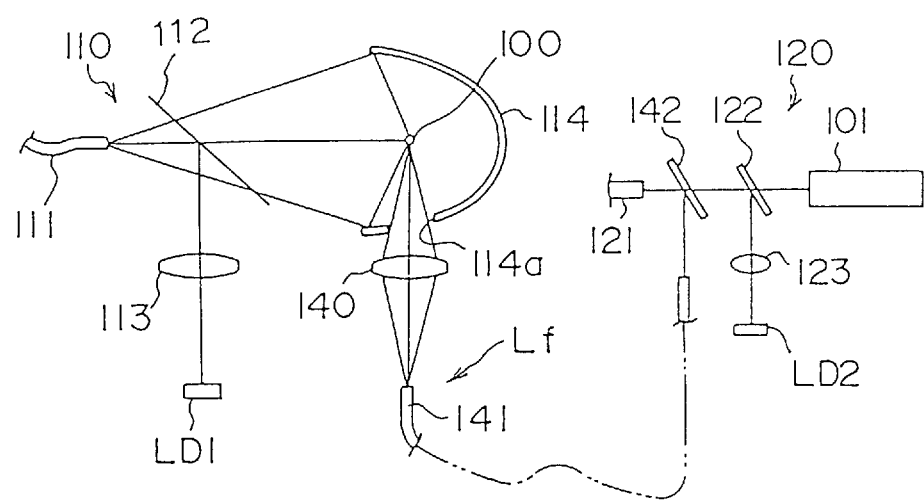
FIG. 13 is an explanatory view of an important portion of an optical system showing a fifth embodiment of the present invention.

For example, as shown in FIG. 13, it may be arranged such that the concave reflecting mirror 114 of the first embodiment is provided with a light outlet hole 114a, and the light coming out of this light outlet hole 114a is used as the aiming light. At this time, the light coming out of the light outlet hole 114a is made incident to the one end 121a of the optical fiber 121 through the focusing lens 140, the optical fiber 141, and the half mirror 142 of the light guide means Lf, and then irradiated, as the aiming light, to the eye fundus Ef from the other end of the optical fiber 121.

In this embodiment, the intensity of the laser emission of the argon laser unit 101 can be controlled only in view of the level required for optical solidification, and the argon laser unit 101 is not required to be used for irradiating the aiming light when a visual light observation is undergoing. Other functions are the same to those of the first embodiment.

[Sixth Embodiment]

Figure 14:
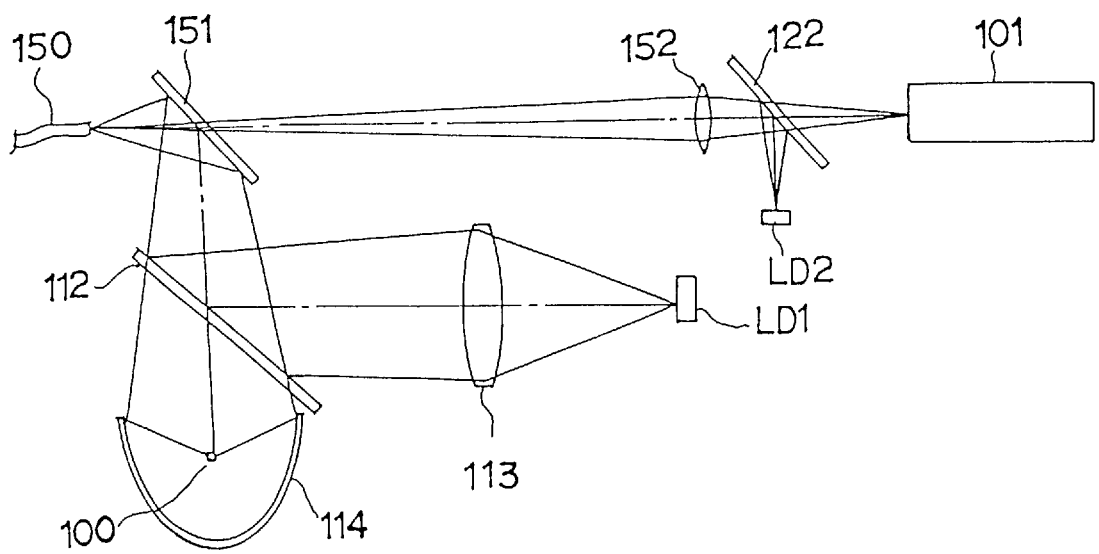
FIG. 14(a) is an explanatory view of an important portion of an optical system showing a sixth embodiment of the present invention.
FIG. 14(b) is an explanatory view showing a relation between a luminous flux emitted from the other end of an optical fiber of FIG. 14(a) and the eye fundus.
Figure 14:
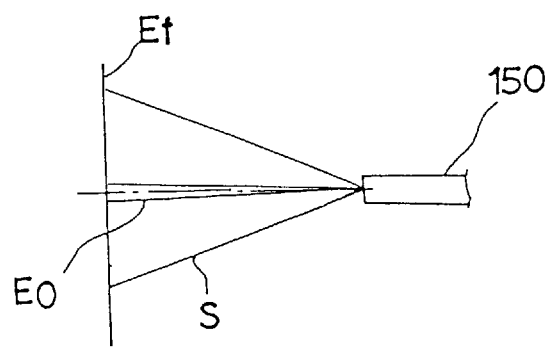

FIG. 14 shows a sixth embodiment of the present invention. In this embodiment, the eye fundus illumination light, the aiming light and the optical solidification laser beam are guided to the eye fundus Ef merely by a single optical fiber 150.

In this embodiment, a half mirror 151 and a dichroic mirror 122 (optical path splitting member) are disposed at a midway of an optical path between the argon laser unit 101 and the optical fiber 150. Moreover, a focusing lens 152 having a long focal point is disposed between the mirrors 151 and 122.

The visible illumination light from the halogen lamp 100 is reflected and gathered by the concave reflecting mirror 114 and allowed to pass through the dichroic mirror 112. Then, it is made incident to the optical fiber 150 by the half mirror 151.

After being reflected by the dichroic mirror 122, the light from the laser diode LD1 is allowed to pass through the half mirror 151 while being gathered by the focusing lens 152. Then, it is made incident to the optical fiber 150.

With this construction, as shown in FIG. 14(a), the aiming light, etc. from the argon laser unit 101 or the laser diode LD2 is made incident to one end of the optical fiber 150 by the focusing lens 152 having a long focal point, the aiming light emitted from the other end of the optical fiber 150 is irradiated, like a spot illumination, to the eye fundus Ef in a narrow condition. On the other hand, the illumination light from the halogen lamp 100 and the laser diode LD1 is gathered by the concave reflecting mirror 114 or focusing lens 113 having a short focal point and then made incident to one end of the optical fiber 150 as shown in FIG. 14(a). Therefore, the illumination luminous flux S emitted from the other end of the optical fiber 150 illuminates a wide range of the eye fundus Ef as shown in FIG. 14(b).

Also in this embodiment, since the laser diodes LD1 and LD2, the halogen lamp 100, the argon laser unit 101, etc. are controlled in the same manner as the second embodiment, description of the control is omitted.

According to this embodiment, since it suffices that only one optical fiber 150 is used as a light guiding fiber, load incurred to the eye E can be reduced during the operation.

Also in this case, when the aiming light is used as a laser optical solidification of the eye fundus Ef, the distal end of the optical fiber 150 is brought closely to the eye fundus Ef.

By separating the distal end of the optical fiber 150 sufficiently away from the eye fundus Ef, the aiming light can also be used as an eye fundus illumination light.

[Other Embodiment]

In the embodiments so far described, although the eye fundus are observed under the visible light and a deep portion of the eye fundus is observed under the infrared fluorescent light, it may be arranged such that the eye fundus is observed under the infrared light and the inner side of the upper skin (or epithelium) layer of the retina of the eye fundus is observed under the visible fluorescent light.

More specifically, in the first embodiment, a visible fluorescent light excitation exciter filter is withdrawably inserted between the concave reflecting mirror 114 and the dichroic mirror 112, and a barrier filter for passing a visible light of a visible fluorescent light wavelength is likewise withdrawably inserted between the dichroic mirror 80 and the quick return half mirror 81 of the optical systems 2a and 2b.

It may also be arranged such that the wavelength of the laser beam of the laser diode LD1 is the same to that of the laser beam of the laser diode LD2, and the eye fundus is illuminated by the illumination light from the laser diode LD1 and the predetermined part of the eye fundus is illuminated by an aiming spot light from the laser diode LD2, the illuminated condition by the infrared light being taken by the TV cameras 91 and 91' of FIG. 8, the illuminated condition of the eye fundus as well as the aiming condition being observed, using the monitor TV 67 and the liquid crystal displays 93 and 93' of the embodiment of FIG. 8.

In that case, the insertion and withdrawal of the exciter filter to and from the optical path is performed in association with the insertion and withdrawal of the barrier filter to and from the optical path.

Although the dichroic mirrors 80 and 80' pass the infrared laser luminous flux of a wavelength emitted from the laser diode LD1 and reflect the laser luminous flux of a wavelength emitted from the laser diode LD2, the present invention is not necessarily limited to this. For example, the optical characteristics may be set such that the dichroic mirrors 80 and 80' pass the visible flux therethrough and reflect the infrared light, and an infrared fluorescent light barrier filter may be withdrawably inserted into a midway of the optical path between the dichroic mirrors 80 and 80' and the TV cameras 91 and 91'. In that case, observation can be selectively made such that the eye fundus is observed under the infrared light and a deep portion of the eye fundus is observed under the infrared fluorescent light.

Since the present invention is constructed in the manner as described above, when an operation is undergone for a diseased part of the fundus of the eye to be tested, a plurality of light each having a different wavelength necessary for observation and treatment can be guided to the eye fundus. Among the light having different wavelengths, the infrared fluorescent excitation light and the visible fluorescent excitation light are used, thereby enabling to make it easy to observe and treat the diseased part at the inner side of the upper skin (or epithelium) layer of the retina of the eye fundus.

What is claimed is:

1. A surgical stereoscopic microscope comprising an illumination optical system for guiding light emitted from a light source to a predetermined part to be illuminated, and right and left optical systems each having an occular lens for observation of the predetermined part and located at one end of an optical path having a variable lens and an eye width adjusting prism, light reflected from said predetermined part entering the right and left optical systems, said surgical stereoscopic microscope further comprising:

an electronic image pick-up optical system disposed along the optical path of each of said right and left optical systems, said electronic image pick-up optical system including light separation means for extracting only infrared fluorescent light entering said right and left optical systems from said predetermined part from between the variable lens and the eye width adjusting prism of the optical path of each of said right and left optical systems;

an infrared fluorescent light image pick-up TV camera to receive light reflected from said predetermined part and guided by said electronic image pick-up optical systems;

a pair of display means for displaying an image of said predetermined part formed on said infrared TV camera simultaneously with observation of the predetermined part at the ocular lenses of said right and left optical systems; and movable mirror means, located between the variable lens and the eye width adjusting prism of the optical path of each of said right and left optical systems, for guiding an infrared fluorescent light image of said predetermined part displayed on said display means to ocular lenses of said right and left optical systems when said movable mirror means is inserted in each optical path of said right and left optical systems, so that the infrared fluorescent light image of said predetermined part is presented at the ocular lenses of both said left and right optical systems, and simultaneously, a visible light image of said predetermined part is presented at the ocular lenses of both said left and right optical systems, whereby the infrared fluorescent light image and the visible light image of said predetermined part are superimposed upon each other and stereoscopically observed.

2. A surgical stereoscopic microscope according to claim 1, wherein said light source includes a white illumination light source for emitting a white illumination light beam and an infrared illumination light source for emitting an infrared excitation light beam, and visible and infrared laser light sources each having a different wavelength for illuminating said predetermined part, the light beams emitted from said white illumination light source, infrared illumination light source, visible laser light source, and infrared laser light source being guided to said predetermined part by an optical fiber.

3. A surgical stereoscopic microscope according to claim 1, wherein said light source includes a visible laser light source and an infrared laser light source each having a different wavelength for illuminating said predetermined part, the light beams emitted from said visible laser light source and infrared laser light source being guided to said predetermined part by an optical fiber.

4. A surgical stereoscopic microscope according to claim 3, wherein at least one of said laser light sources is controlled by a control circuit to selectively emit an aiming light beam having a low emissive intensity for illuminating said predetermined part or a treatment laser light beam having a high emissive intensity for treating said predetermined part.

5. A surgical stereoscopic microscope comprising an illumination optical system for guiding light emitted from a light source to a predetermined part of an eye fundus to be illuminated, and right and left optical systems each having an occular lens for observation of the predetermined part and located at one end of an optical path having a variable lens and an eye width adjusting prism, light reflected from said predetermined part entering the right and left optical systems, said surgical stereoscopic microscope further comprising:

an electronic image pick-up optical system disposed along the optical path of each of said right and left optical systems, said electronic image pick-up optical system including light separation means for extracting only infrared fluorescent light entering said right and left optical systems from said predetermined part from between the variable lens and the eye width adjusting prism of the optical path of each of said right and left optical systems;

an infrared fluorescent light image pick-up TV camera to receive light reflected from said predetermined part and guided by said electronic image pick-up optical systems;

a pair of display means for displaying an image of said predetermined part formed on said infrared TV camera in simultaneously with observation of the predetermined part at the ocular lenses of said right and left optical systems; and means, disposed between the variable lens and the eye width adjusting prism of the optical path of each of said right and left optical systems, for guiding an infrared fluorescent light image of said predetermined part displayed on said display means to the ocular lenses of said right and left optical systems so that the infrared fluorescent light image of said predetermined part is stereoscopically observed.

6. A surgical stereoscopic microscope according to claim 5, wherein said light source includes a visible laser light source and an infrared laser light source each having a different wavelength for illuminating said predetermined part, the light beams emitted from said visible laser light source and infrared laser light source being guided to said predetermined part by an optical fiber.

7. A surgical stereoscopic microscope according to claim 5, wherein said light source includes a white illumination light source for emitting a white illumination light beam and an infrared illumination light source for emitting an infrared excitation light beam, and visible and infrared laser light source each having a different wavelength for illuminating said predetermined part, the light beams emitted from said white illumination light source, infrared illumination light source, visible laser light source, and infrared laser light source being guided to said predetermined part by an optical fiber.

* * * * *